US011154275B2

(12) United States Patent
Gu et al.

(10) Patent No.: US 11,154,275 B2
(45) Date of Patent: Oct. 26, 2021

(54) ULTRASONIC PROBE, METHOD FOR CONTROLLING THE ULTRASONIC PROBE, AND ULTRASONIC IMAGING APPARATUS INCLUDING THE ULTRASONIC PROBE

(71) Applicant: SAMSUNG MEDISON CO., LTD., Gangwon-do (KR)

(72) Inventors: Jin Ho Gu, Yongin-si (KR); Gil-Ju Jin, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 412 days.

(21) Appl. No.: 15/478,897

(22) Filed: Apr. 4, 2017

(65) Prior Publication Data

US 2018/0064416 A1 Mar. 8, 2018

(30) Foreign Application Priority Data

Sep. 6, 2016 (KR) .................. 10-2016-0114260

(51) Int. Cl.
*A61B 8/00* (2006.01)
*A61B 8/14* (2006.01)

(52) U.S. Cl.
CPC ............... *A61B 8/429* (2013.01); *A61B 8/14* (2013.01); *A61B 8/467* (2013.01); *A61B 8/54* (2013.01); *A61B 8/4405* (2013.01); *A61B 8/4472* (2013.01); *A61B 8/4483* (2013.01); *A61B 8/461* (2013.01)

(58) Field of Classification Search
CPC .. A61B 8/14; A61B 8/467; A61B 8/54; A61B 8/4405; A61B 8/4472; A61B 8/4483
See application file for complete search history.

(56) References Cited

U.S. PATENT DOCUMENTS

| 5,897,503 A | 4/1999 | Lyon et al. |
| 6,436,050 B2 | 8/2002 | Garrison et al. |
| 6,511,427 B1* | 1/2003 | Sliwa, Jr. ............. A61B 5/4869 600/438 |
| 8,827,909 B2 | 9/2014 | Kierulf et al. |
| 2002/0138007 A1* | 9/2002 | Nguyen-Dinh ........ A61B 8/467 600/459 |
| 2007/0016057 A1 | 1/2007 | Dallago et al. |

(Continued)

FOREIGN PATENT DOCUMENTS

| JP | 2013-212184 A | 10/2013 |
| KR | 10-2014-0128504 A | 11/2014 |

*Primary Examiner* — Angela M Hoffa
(74) *Attorney, Agent, or Firm* — Morgan, Lewis & Bockius LLP

(57) ABSTRACT

An ultrasonic probe, a method for controlling the same, and an ultrasonic imaging apparatus including the same are disclosed. The ultrasonic probe includes a housing; a first contact sensing portion located at one position of an outer surface of the housing, and configured to detect contact; and a second contact sensing portion located at a different position from the first contact sensing portion, and configured to detect contact. A combination of contact sensing results obtained from the first contact sensing portion and the second contact sensing portion is determined such that an operation corresponding to the determined combination of the contact sensing results is carried out.

19 Claims, 11 Drawing Sheets

(56) References Cited

U.S. PATENT DOCUMENTS

| | | | |
|---|---|---|---|
| 2010/0191120 A1* | 7/2010 | Kraus | A61B 8/481 |
| | | | 600/459 |
| 2011/0112405 A1* | 5/2011 | Barthe | A45D 44/005 |
| | | | 600/459 |
| 2012/0165622 A1* | 6/2012 | Rodr Guez Ib Nez | A61B 5/00 |
| | | | 600/301 |
| 2013/0158411 A1* | 6/2013 | Miyasaka | A61B 8/54 |
| | | | 600/472 |
| 2015/0065881 A1 | 3/2015 | Cho et al. | |
| 2015/0286309 A1 | 10/2015 | Chang et al. | |

* cited by examiner

FIG. 11

| COMBINATION OF CONTACT SENSING RESULTS | EXECUTION OPERATION |
|---|---|
| FIRST CONTACT SENSING PORTION + SECOND CONTACT SENSING PORTION | ROI SETTING |
| FIRST CONTACT SENSING PORTION + THIRD CONTACT SENSING PORTION | TGC/LGC CONTROL |
| FIRST CONTACT SENSING PORTION + SECOND CONTACT SENSING PORTION + THIRD CONTACT SENSING PORTION | FREEZE |

⋮

ULTRASONIC PROBE, METHOD FOR CONTROLLING THE ULTRASONIC PROBE, AND ULTRASONIC IMAGING APPARATUS INCLUDING THE ULTRASONIC PROBE

CROSS-REFERENCE TO RELATED APPLICATION

This application claims the benefit of Korean Patent Application No. 10-2016-0114260, filed on Sep. 6, 2016 in the Korean Intellectual Property Office, the disclosure of which is incorporated herein by reference.

BACKGROUND

1. Field

Embodiments of the present disclosure relate to an ultrasonic probe, a method for controlling the ultrasonic probe, and an ultrasonic imaging apparatus including the ultrasonic probe.

2. Description of the Related Art

An ultrasonic diagnostic apparatus applies an ultrasonic signal from the surface of an object (for example, a human body) to a target site inside of the body of the object, and non-invasively acquires tomograms of soft tissues or images regarding blood flow upon receiving reflected echo signals.

The ultrasonic diagnostic apparatus has compact size and low price, displays a diagnostic image in real time, as compared to other image diagnostic apparatuses, for example, an X-ray diagnostic apparatus, a computed tomography (CT) scanner, a magnetic resonance imaging (MRI) apparatus, and a nuclear medical diagnostic apparatus. In addition, since the ultrasonic diagnostic apparatus does not cause radiation exposure, the ultrasonic diagnostic apparatus is inherently safe. Accordingly, the ultrasonic diagnostic apparatus has been widely utilized for cardiac, abdominal, and urologic diagnosis as well as obstetric and gynecological diagnosis.

The ultrasonic diagnostic apparatus includes an ultrasonic probe for transmitting ultrasonic signals to a target object so as to acquire an ultrasonic image of the target object, and receiving ultrasonic echo signals reflected from the target object.

In recent times, the ultrasonic probe configured to acquire ultrasonic images from the target object has also been used as an input portion for inputting various control commands to the ultrasonic imaging apparatus.

SUMMARY

Therefore, it is an aspect of the present disclosure to provide an ultrasonic probe composed of a plurality of contact sensing portions capable of detecting user contact, a method for controlling the ultrasonic probe, and an ultrasonic imaging apparatus including the ultrasonic probe.

It is another aspect of the present disclosure to provide an ultrasonic probe configured to determine a combination of the contact sensing results of a plurality of contact sensing portions and to operate in response to the combination of the contact sensing results, a method for controlling the ultrasonic probe, and an ultrasonic imaging apparatus including the ultrasonic probe.

In accordance with one aspect of the present disclosure, an ultrasonic probe includes: a housing; a first contact sensing portion located at one position of an outer surface of the housing, and configured to detect contact; and a second contact sensing portion located at a different position from the first contact sensing portion, and configured to detect contact. A combination of contact sensing results obtained from the first contact sensing portion and the second contact sensing portion is determined such that an operation corresponding to the determined combination of the contact sensing results is carried out.

The first contact sensing portion and the second contact sensing portion may contact a user, such that the first contact sensing portion and the second contact sensing portion are electrically connected to each other through a human body of the user.

The ultrasonic probe may further include at least one of: a third contact sensing portion formed between the first contact sensing portion and the second contact sensing portion, and configured to include a plurality of sub contact sensing portions sequentially formed; and a fourth contact sensing portion including a lens formed of an electrically conductive material, and configured to detect presence or absence of the lens.

The operation corresponding to a combination of contact sensing results of at least two from among the first contact sensing portion, the second contact sensing portion, the third contact sensing portion, and the fourth contact sensing portion may be carried out.

At least one of the first contact sensing portion, the second contact sensing portion, and the third contact sensing portion may include at least two sub regions, each of which is formed of an electrically conductive material and detects presence or absence of contact.

The operation corresponding to the combination of the contact sensing results may include at least one of Region of Interest (ROI) selection regarding a target object, ultrasonic image freeze, ultrasonic image capture, measurement data acquisition, Time Gain Compensation (TGC) control, Lateral Gain Compensation (LGC) control, ultrasonic image depth control, 2D/3D image conversion, focusing, and probe automatic selection.

The combination of the contact sensing results may be determined using at least one of a contact position, a contact time, and an order of contacts.

The operation corresponding to the combination of the contact sensing results may be established by a user or may be predetermined by the user.

The surfaces of at least two of the first contact sensing portion, the second contact sensing portion, the third contact sensing portion, and the fourth contact sensing portion may be formed of different materials.

The first contact sensing portion, the second contact sensing portion, the third contact sensing portion, and the fourth contact sensing portion may be visually distinguished from one another using at least one of a symbol, a letter, a figure, a shape, a color, and a solid structure.

In accordance with another aspect of the present disclosure, a method for controlling an ultrasonic probe includes: detecting a first contact in a first region of an outer surface of the ultrasonic probe; detecting a second contact in a second region different from one position of the outer surface of the ultrasonic probe; determining a combination of contact sensing results between the first contact and the second contact; and controlling the ultrasonic probe to perform an operation corresponding to the determined combination of the contact sensing results.

The method may further include: detecting a third contact in a region disposed between the first region and the second region.

The method may further include: detecting a fourth contact using a lens formed of an electrically conductive material.

The method may further include: determining a combination of contact sensing results of at least two from among the first contact, the second contact, the third contact, and the fourth contact, and performing an operation corresponding to the determined combination.

The controlling of the ultrasonic probe to perform the operation corresponding to the determined combination of the contact sensing results may include at least one of: selecting a Region of Interest (ROI) regarding a target object; freezing an ultrasonic image; capturing the ultrasonic image; acquiring measurement data; controlling Time Gain Compensation (TGC); controlling Lateral Gain Compensation (LGC); controlling depth of the ultrasonic image; performing 2D/3D image conversion; focusing the ultrasonic image; and automatically selecting a probe.

The combination of the contact sensing results may be determined using at least one of a contact position, a contact time, and an order of contacts.

The operation corresponding to the combination of the contact sensing results may be established by a user.

The first region of the outer surface of the ultrasonic probe and the second region different from one position of the outer surface of the ultrasonic probe may be formed of different materials.

The first region of the outer surface of the ultrasonic probe and the second region different from one position of the outer surface of the ultrasonic probe may be visually distinguished from each other using at least one of a symbol, a letter, a figure, a shape, a color, and a solid structure.

In accordance with another aspect of the present disclosure, an ultrasonic imaging apparatus includes an ultrasonic probe and a controller. The ultrasonic probe includes a housing; a first contact sensing portion located at one position of an outer surface of the housing, and configured to detect contact; and a second contact sensing portion located at a different position from the first contact sensing portion, and configured to detect contact. The controller may control the ultrasonic to determine a combination of contact sensing results obtained from the first contact sensing portion and the second contact sensing portion in such a manner that an operation corresponding to the determined combination of the contact sensing results is carried out.

BRIEF DESCRIPTION OF THE DRAWINGS

These and/or other aspects of the invention will become apparent and more readily appreciated from the following description of the embodiments, taken in conjunction with the accompanying drawings of which:

FIG. 11 illustrates exemplary operations corresponding to the contact sensing results of the plurality of contact portions.

DETAILED DESCRIPTION

Hereinafter, the above and other objects, specific advantages, and novel features of the present invention will become apparent from the following description of embodiments, given in conjunction with the accompanying drawings. Reference will now be made in detail to the embodiments of the present invention, examples of which are illustrated in the accompanying drawings. Wherever possible, the same reference numbers will be used throughout the drawings to refer to the same or like parts. In the following description, known functions or structures, which may confuse the substance of the present invention, are not explained. It will be understood that, although the terms first, second, etc. may be used herein to describe various elements, components, regions, layers and/or sections, these elements, components, regions, layers and/or sections should not be limited by these terms.

An ultrasonic probe, a method for controlling the ultrasonic probe, and an ultrasonic imaging apparatus including the ultrasonic probe according to the embodiments of the present disclosure will hereinafter be described with reference to FIGS. 1 to 11.

Figure 1:
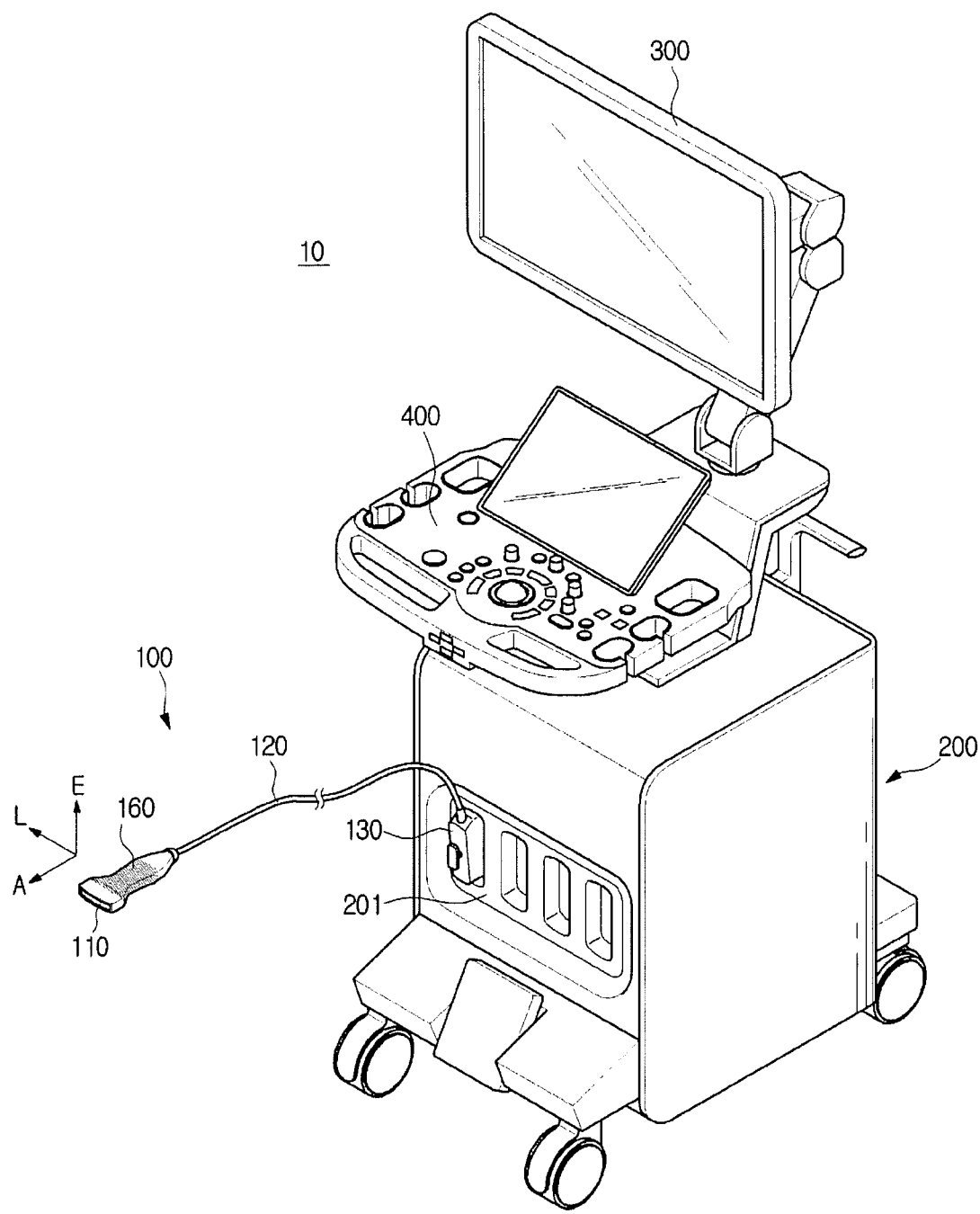
FIG. 1 is a perspective view illustrating an external appearance of an ultrasonic imaging apparatus according to an embodiment of the present disclosure.
Figure 2:
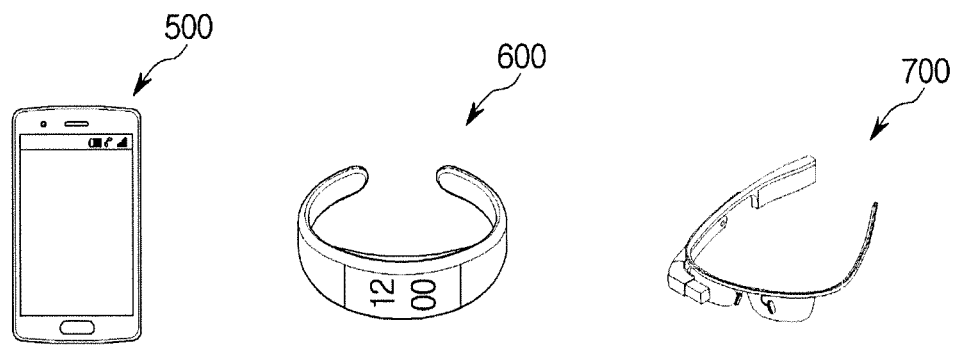
FIG. 2 is a view illustrating external devices configured to wirelessly communicate with the ultrasonic imaging apparatus.

FIG. 1 is a perspective view illustrating an external appearance of an ultrasonic imaging apparatus according to an embodiment of the present disclosure. FIG. 2 is a view illustrating external devices configured to wirelessly communicate with the ultrasonic imaging apparatus.

Referring to FIG. 1, the ultrasonic imaging apparatus 10 may include an ultrasonic probe 100 and a main body 200. The ultrasonic probe 100 may transmit an ultrasonic signal to a target object, may receive an echo ultrasonic signal from the target object, and may convert the received echo ultrasonic signal into an electrical signal to obtain an ultrasonic image. The main body 200 may generate an ultrasonic image on the basis of the ultrasonic signal. The main body 200 may be connected to the ultrasonic probe 100 over a wireless communication network or a wired communication network. The main body 200 may be a workstation including a display 300 and an input portion 400.

Figure 8:
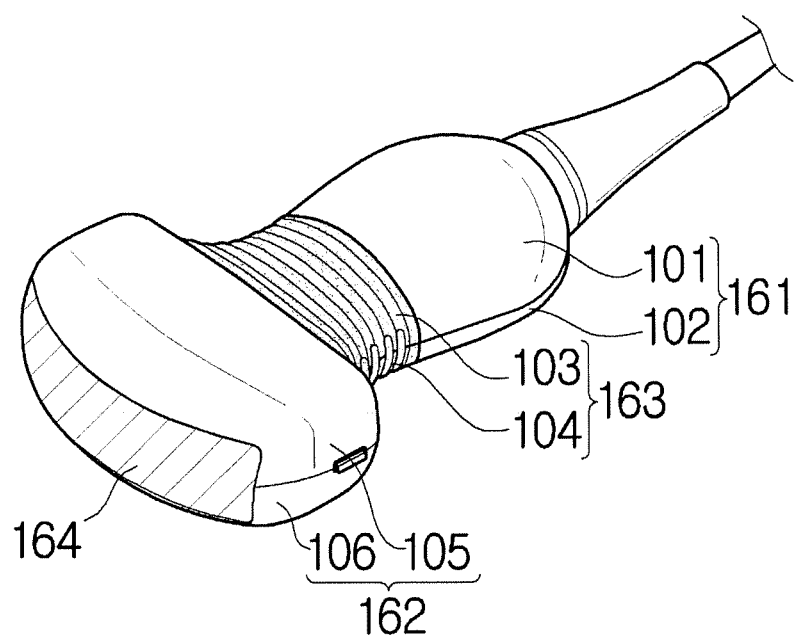
FIG. 8 is a view illustrating an ultrasonic probe including the plurality of contact portions.

The main body 200 may transmit and receive various kinds of information to and from an external device over a wired or wireless communication network. The external device may denote a device including a display for displaying information and a communication module for implementing wireless communication, and may be all kinds of devices capable of communicating with the ultrasonic imaging apparatus 10. The external device 300 may be implemented as any one of a laptop, a desktop computer, and a tablet PC, or may be implemented as a smartphone as shown in FIG. 8. For example, as shown in FIG. 2, the external device may be any of a smartphone 500, a PDA, a tablet PC, a personal computer (PC), a watch detachably coupled to a user's body, and glasses-type wearable terminals 600 and 700.

The ultrasonic imaging apparatus 10 may be used for ultrasonic diagnosis in hospitals or the like as shown in FIG. 1. However, the scope or spirit of the ultrasonic imaging apparatus 10 is not limited to FIG. 1.

For example, the ultrasonic imaging apparatus 10 may be implemented as any one of a laptop, a desktop computer, and a tablet PC, or may be implemented as a smartphone 500 as shown in FIG. 2. The ultrasonic imaging apparatus 10 may include a mobile terminal such as a PDA, a watch 600 detachably coupled to the user's body, and a glasses-type wearable terminal 700.

However, the ultrasonic imaging apparatus 10 is not limited thereto, and may include any device which includes a communicator therein so as to communicate with the external device over the wireless communication network and may display ultrasonic images through a display without departing from the scope or spirit of the present disclosure.

In this case, although a target object (ob) may be a living body of a human or an animal, and a target site may be tissue in the living body, such as blood vessels, bones, muscles, or the like, the scope or spirit of the present invention is not limited thereto. If necessary, all kinds of objects, internal structures of which can be imaged by the ultrasonic imaging apparatus 10, may be used as the target object without departing from the scope or spirit of the present invention.

The ultrasonic probe 100 may include a transducer module 110, a male connector 130, and a cable 120. The transducer module 110 may be contained in a housing (h), may irradiate a target object (ob) with ultrasonic waves, may receive echo ultrasonic waves reflected from the target object (ob), and may perform conversion between an electrical signal and ultrasonic waves. The male connector 130 may be physically connected to a female connector of the main body 200, and may transmit and receive signals to and from the main body 200. The cable 120 may connect the male connector 130 to the transducer module 110. A surface of the ultrasonic probe 100 may be formed of an electrically conductive material.

Therefore, the surface of the ultrasonic probe 100 may be formed of an electrically conductive material, resulting in occurrence of electrostatic induction through a medium of a human body. Electrostatic electricity flowing on the surface of the ultrasonic probe 100 may be a minute electric current incapable of being recognized by the user. In addition, the ultrasonic probe 100 may include a contact sensing portion 160 configured to detect user contact.

The contact sensing portion 160 may be formed in a plurality of regions of the surface of the ultrasonic probe 100, and may also be formed of an electrically conductive material. Since the contact sensing portion 160 may be formed of an electrically conductive material, the contact sensing portion 160 may detect the presence or absence of user contact using electrostatic electricity induced through a human body of the user, and a detailed description thereof will hereinafter be given with reference to the attached drawings.

According to the above-mentioned principles, the ultrasonic probe 100 may detect the presence or absence of user contact using the contact sensing portion 160. In addition, the ultrasonic probe 100 may determine a combination of the detected user contact and the sensed contact sensing results, and may perform a necessary operation corresponding to the determined result.

A detailed description thereof will hereinafter be described with reference to the attached drawings.

The ultrasonic probe 100 may be connected to at least one of the main body 200 and the external device over a wireless communication network, and may receive various signals needed to control the ultrasonic probe 100 or may transmit analog or digital signals corresponding to the echo ultrasonic signal received by the ultrasonic probe 100.

A wireless communication network may be a communication network configured to support a wireless communication scheme capable of wirelessly transmitting and receiving signals. For example, the wireless communication scheme may include not only a communication scheme (e.g., 3G or 4G communication) for transmitting and receiving radio frequency (RF) signals through a base station (BS), but also all direct communication schemes in which RF signals can be directly communicated between devices located within a predetermined distance. For example, the direct communication schemes may include Wireless LAN, Wi-Fi, Bluetooth, ZigBee, Wi-Fi Direct (WED), Ultra wideband (UWB), Infrared Data Association (IrDA), Bluetooth Low Energy (BLE), Near Field Communication (NGC), etc. without being limited thereto. However, the scope or spirit of the wireless communication schemes is not limited thereto, and may include all kinds of communication networks capable of supporting RF communication between the ultrasonic probe 100 and the main body 200.

An echo ultrasonic signal may be reflected from the target object (ob) to which ultrasonic waves are radiated, and may have various frequency bands or various energy strengths to generate various ultrasonic images according to diagnostic modes.

The transducer module 110 may generate ultrasonic waves or ultrasonic signals according to received AC power. In more detail, the transducer module 110 may receive AC power from an external power-supply device or an internal device (e.g., a battery). A vibrator of the transducer module 110 may vibrate according to the received AC power, and may thus generate ultrasonic waves.

Three directions perpendicular to one another on the basis of the center point of the transducer module 110 may be defined as an axis direction A, a lateral direction L, and an elevation direction E. In more detail, a direction of ultrasonic irradiation is defined as the axis direction A, a direction along which the transducer module 110 forms a column is defined as the lateral direction L, and the remaining direction perpendicular to the directions A and L may be defined as the elevation direction E.

One end of the cable 120 may be connected to the transducer module 110, and the other end of the cable 120 may be connected to the male connector 130, such that the transducer module 110 may be connected to the male connector 130.

The male connector 130 may be connected to the other end of the cable 120, such that the male connector 130 may be physically coupled to the female connector 201 of the main body 200.

The male connector 130 may transmit an electrical signal generated by the transducer module 110 to the female connector 201 physically coupled thereto, or may receive a control signal generated by the main body 200 from the female connector 201.

However, if the ultrasonic probe 100 is implemented as a wireless ultrasonic probe, the cable 120 and the male connector 130 may be omitted, and the ultrasonic probe 100 and the main body 200 may communicate with each other through a separate wireless communication module (not shown) contained in the ultrasonic probe 100, without being limited to the ultrasonic probe 100 of FIG. 1.

The main body 200 may communicate with the ultrasonic probe 100 through at least one of a local area network (LAN) communication module and a mobile communication module.

The LAN communication module may denote a communication module for short-range communication within a predetermined distance. The LAN communication technology may include Wireless LAN, Wi-Fi, Bluetooth, ZigBee, Wi-Fi Direct (WFD), Ultra wideband (UWB), Infrared Data Association (IrDA), Bluetooth Low Energy (BLE), Near Field Communication (NFC), etc. without being limited thereto.

The mobile communication module may transmit and receive radio frequency (RF) signals to and from at least one of a base station (BS), an external terminal, and a server over the mobile communication network. In this case, the RF signal may include various types of data. That is, the main body 200 may transmit and receive signals including various types of data to and from the ultrasonic probe 100 through at least one of the base station (BS) and the server.

For example, the main body 200 may transmit and receive signals including various types of data to and from the ultrasonic probe 100 through the base station (BS) over a mobile communication network such as a 3G or 4G network. The main body 200 may communicate with a hospital server or other in-hospital medical machines connected through a Picture Archiving and Communication System (PACS). In addition, the main body 200 may perform data communication according to medical digital imaging and Digital Imaging and Communications in Medicine (DICOM) standard, without being limited thereto.

Besides, the main body 200 may communicate with the ultrasonic probe 100 over a wired communication network.

The wired communication network may be a communication network through which signals may be transmitted and received by wire. In accordance with one embodiment, the main body 200 may communicate with the ultrasonic probe 100 over a wired communication network, for example, Peripheral Component Interconnect (PCI), PCI-express, Universe Serial Bus (USB), etc., without being limited thereto.

The ultrasonic probe will hereinafter be described with reference to the attached drawings.

Figure 3:
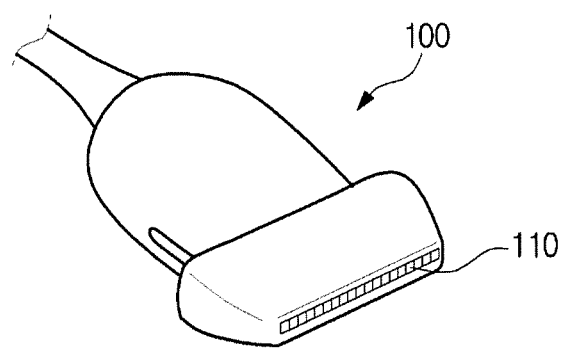
FIG. 3 is a view illustrating an ultrasonic probe including a one-dimensional (1D) array transducer.
Figure 4:
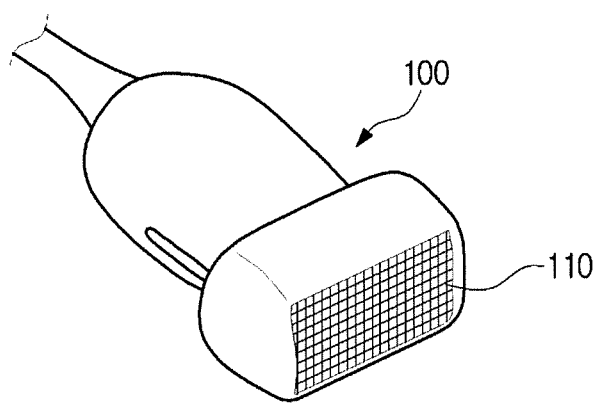
FIG. 4 is a view illustrating an ultrasonic probe including a two-dimensional (2D) array transducer.

FIG. 3 is a view illustrating an ultrasonic probe including a one-dimensional (1D) array transducer. FIG. 4 is a view illustrating an ultrasonic probe including a two-dimensional (2D) array transducer.

Referring to FIGS. 3 and 4, the ultrasonic probe 100 may contact the surface of a target object, and may transmit and receive ultrasonic signals to and from the target object.

In more detail, the ultrasonic probe 100 may transmit an ultrasonic signal to a target site contained in the target object according to a transmission signal received from the main body, may receive the echo ultrasonic signal reflected from the target site, and may transmit the received echo ultrasonic signal to the main body. In this case, although the echo ultrasonic signal may be an ultrasonic signal acting as a radio frequency (RF) signal reflected from the target object, the scope or spirit of the echo ultrasonic signal is not limited thereto, and the echo ultrasonic signal may include all kinds of signals obtained by reflection of the ultrasonic signal transmitted to the target object.

Meanwhile, the target object may be a living body of a human or an animal, without being limited thereto. If necessary, all kinds of objects, internal structures of which can be imaged by ultrasonic signals, may be used as the target object without departing from the scope or spirit of the present invention.

The ultrasonic probe 100 may include a transducer array for converting an electrical signal into an ultrasonic signal and vice versa to transmit ultrasonic signals to the interior of the target object. The transducer array may include one or more transducer elements.

The ultrasonic probe 100 may generate an ultrasonic signal through the transducer array, may transmit the ultrasonic signal to a target site contained in the target object, and may receive the echo ultrasonic signal reflected from the target site through the transducer array.

If the echo ultrasonic signal arrives at the transducer array, the transducer array may vibrate at a predetermined frequency corresponding to a frequency of the echo ultrasonic signal, and may output an AC current having a frequency corresponding to a vibration frequency of the transducer array. Therefore, the transducer array may convert the received echo ultrasonic signal into an echo signal indicating a predetermined electrical signal.

Meanwhile, the transducer array may be a 1D array or a 2D array. In accordance with one embodiment, the transducer module 110 may include the 1D transducer array as shown in FIG. 1.

Respective transducer elements constructing the 1D transducer array may convert ultrasonic signals into electric signals and vice versa. For this purpose, the transducer element may include a magnetostrictive ultrasonic transducer using magnetostrictive effects of a magnetic material, a piezoelectric ultrasonic transducer using piezoelectric effects of a material, and a piezoelectric micromachined ultrasonic transducer (pMUT). If necessary, the transducer element may also include a capacitive micromachined ultrasonic transducer (cMUT) to transmit and receive ultrasonic waves using vibration of several hundred or several thousand micromachined thin films.

Meanwhile, the transducer module 110 may be arranged in a linear shape as shown in FIG. 3, or may also be arranged in a convex shape as necessary. The linear-shaped transducer module and the convex-shaped transducer module have the same basic operation principles in the ultrasonic probe 100. However, in the case of using the ultrasonic probe 100 including the convex-shaped transducer module 110, the ultrasonic signal emitted from the transducer module 110 is formed in a fan shape, such that an ultrasonic image to be generated may also be formed in a fan shape.

In another example, the transducer module 110 may include a 2D transducer array as shown in FIG. 4. If the transducer module 110 includes the 2D transducer array, the interior of the target object may be 3D-imaged. Although the transducer array of the ultrasonic probe 100 is one-dimensionally arranged, the ultrasonic probe 100 may acquire volume information of the interior of the target object by mechanically moving the 1D transducer array, the ultrasonic probe 100 may transmit the echo ultrasonic signal capable of generating a three-dimensional (3D) ultrasonic image to the main body 200.

The respective transducer elements constructing the 2D transducer array are identical to the transducer elements constructing the 1D transducer array, and as such a detailed description thereof will herein be omitted for convenience of description.

The ultrasonic probe, the ultrasonic imaging apparatus including the same, and internal constituent elements of the ultrasonic imaging apparatus according to the embodiments will hereinafter be described with reference to the attached drawings.

Figure 5:
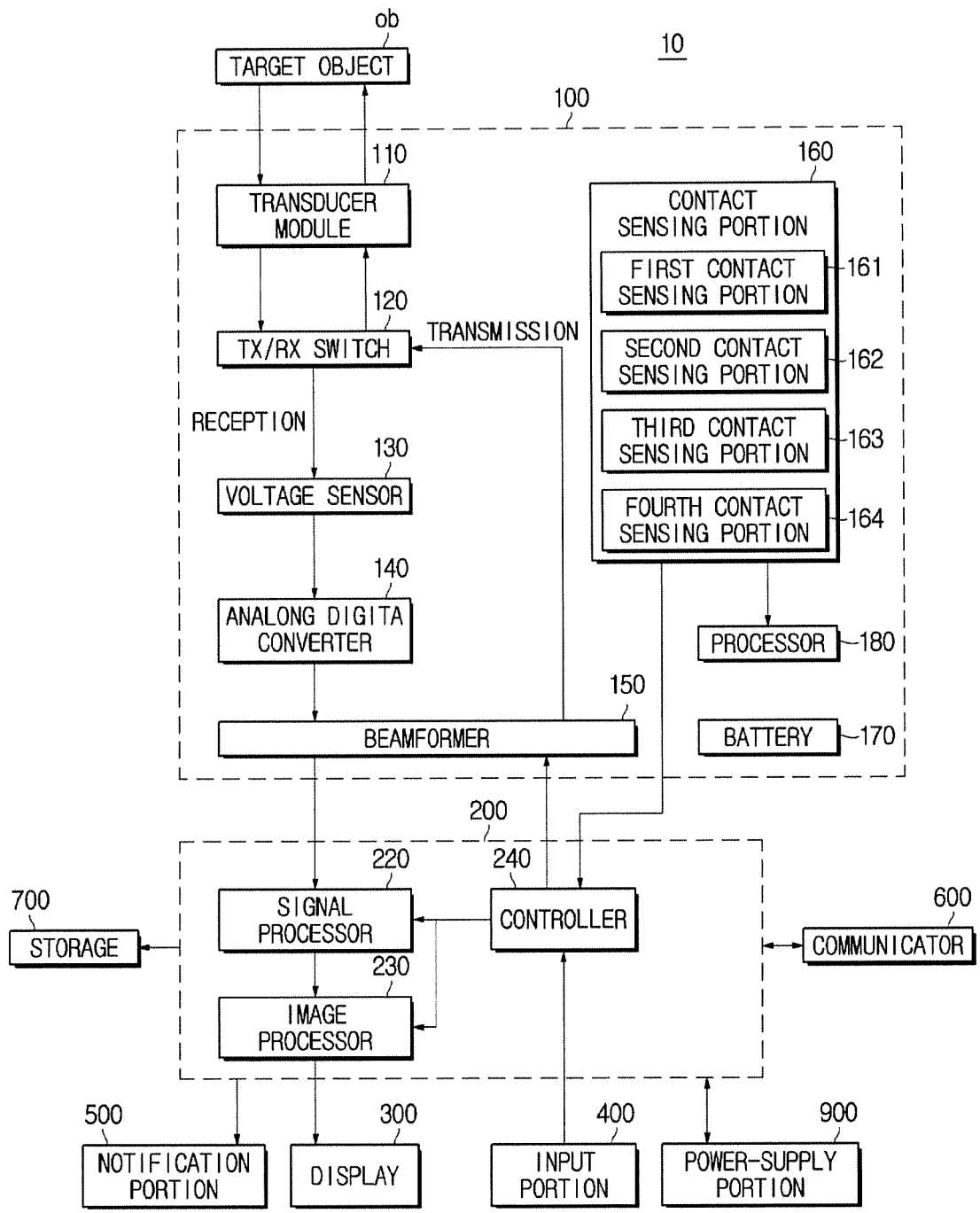
FIG. 5 is a block diagram illustrating an ultrasonic imaging apparatus.
Figure 6:
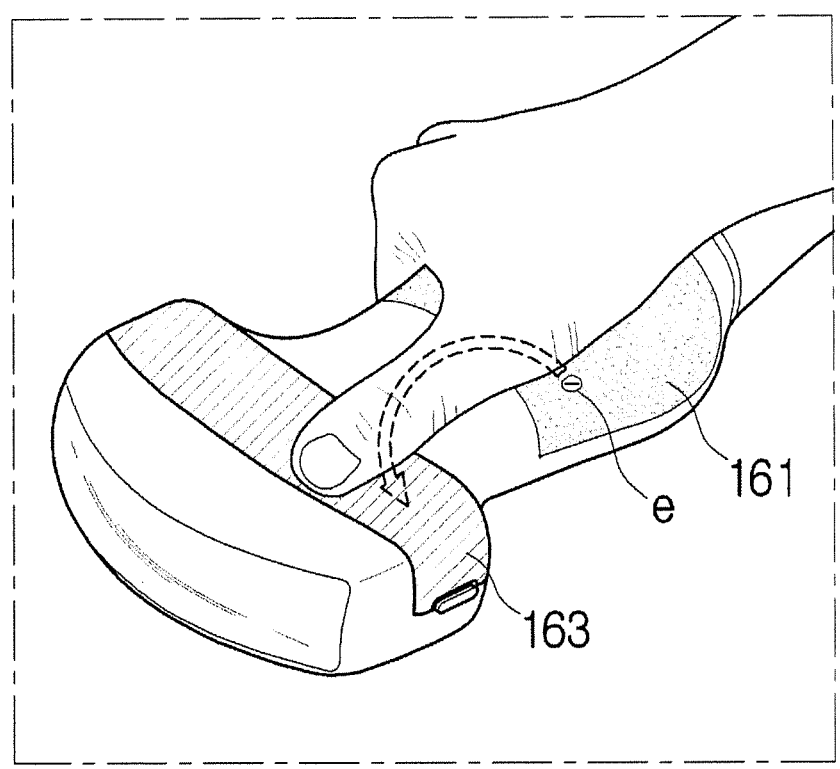
FIG. 6 is a conceptual diagram illustrating a method for sensing contact generated from the plurality of contact portions.
Figure 7:
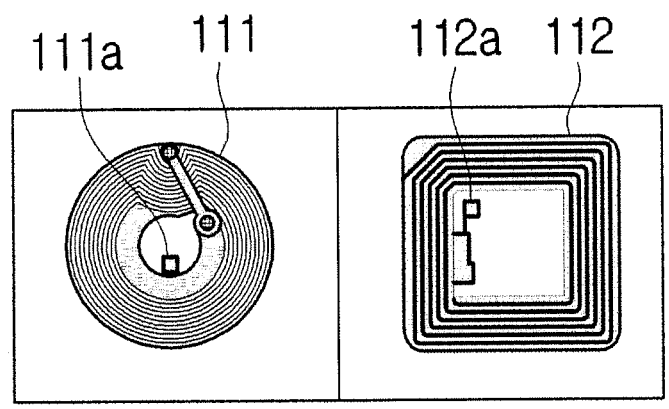
FIG. 7 is a view illustrating the plurality of contact portions.

FIG. 5 is a block diagram illustrating the ultrasonic imaging apparatus. FIG. 6 is a conceptual diagram illustrating a method for sensing contact generated from the plurality of contact portions. FIG. 7 is a view illustrating the plurality of contact portions. FIG. 8 is a view illustrating the ultrasonic probe including the plurality of contact portions.

The ultrasonic probe 100 including a contact sensing portion 160 and the ultrasonic imaging apparatus 100 including the ultrasonic probe 100 will hereinafter be described with reference to FIGS. 5 to 8.

Referring to FIGS. 5 to 8, the ultrasonic probe 100 may further include a beamformer 150, a transmission/reception (Tx/Rx) switch 120, a voltage sensor 130, an Analog-to-Digital Converter (ADC) 140, contact sensing portions 160, a battery 170, and a processor 180, which are contained in the housing (h). The ultrasonic probe 100 may be formed of an electrically conductive material. For example, the ultrasonic probe 100 may be formed of an electrically conductive plastic material formed by mixing fine powders (each having a diameter of about 0.1 μm) such as copper (Cu), silver (Ag), carbon (C), etc. with various plastic materials, or may be formed of an electrically conductive fiber, etc. formed by mixing conductive carbon granules with a polymeric material. In addition, the surface of the ultrasonic probe 100 may also be formed of an electrically conductive material.

In addition, when the ultrasonic probe 100 operates with the ultrasonic imaging apparatus 10, the ultrasonic probe 100 may be controlled according to a wired or wireless control scheme. According to the wired control scheme, the ultrasonic probe 100 is electrically coupled to the main body 200 by wire, and all the contact sensing portions 160 may also be connected by wire, such that signal communication is controlled by wire. According to the wireless control scheme, the ultrasonic probe 100 may include a Near Field Communication (NFC) module, such that the ultrasonic probe 100 may wirelessly communicate with the main body 200 through the NFC module.

Upon receiving a control signal of a system controller 240, the Tx/Rx switch 120 may change a current mode to a transmission (Tx) mode during ultrasound irradiation, or may change a current mode a reception (Rx) mode during ultrasound reception.

The voltage sensor 130 may detect an output current of the transducer module 110. For example, the voltage sensor 130 may be implemented as an amplifier for amplifying a voltage according to the detected output current.

In addition, the voltage sensor 130 may further include a pre-amplifier configured to amplify a minute analog signal. A low noise amplifier (LNA) may be used as the pre-amplifier.

The voltage sensor 130 may further include a variable gain amplifier (VGA) (not shown) configured to control a gain value according to an input signal. In this case, although a time gain compensation (TGC) circuit configured to compensate for either a gain according to a focus point or a gain according to a distance to the focus point may be used as a VGA, the scope or spirit of the present disclosure is not limited thereto.

The ADC 140 may convert an analog voltage generated from the voltage sensor 130 into a digital signal.

Although FIG. 5 exemplarily illustrates that the digital signal generated from the ADC 140 is input to a beamformer 150 for convenience of description, it should be noted that an analog signal delayed by the beamformer 150 may also be input to the ADC 140 such that the input order of analog and digital signals is not limited thereto.

Although FIG. 5 exemplarily illustrates the ADC 140 installed in the ultrasonic probe 100, the scope or spirit of the present disclosure is not limited thereto, and the ADC 140 may also be installed in the main body 200 as necessary. In this case, the ADC 140 may convert an analog signal focused by an adder into a digital signal.

The beamformer 150 may focus ultrasonic signals generated from the transducer module 110 onto a single target point of the target object (ob) at the same time as desired by the ultrasonic signals generated from the transducer module 110, or may allocate a proper delay time to radiated ultrasonic signals or received echo ultrasonic signals in a manner that the echo ultrasonic signals reflected from the single target point of the target object (ob) arrive at the transducer module 110.

In the ultrasonic imaging apparatus 10 of FIG. 5, the beamformer 150 may be contained in the ultrasonic probe 100 corresponding to a front end as described above, or may be contained in the main body 200 corresponding to a back end. However, the scope or spirit of the beamformer 150 according to the embodiment is not limited thereto, and it should be noted that all or some constituent elements of the beamformer 150 may be contained in the front end or the back end without departing from the scope or spirit of the present disclosure.

The contact sensing portion 160 may be formed of an electrically conductive material, and may be formed over the ultrasonic probe 100. In addition, the contact sensing portion 160 formed of the electrically conductive material may detect the presence or absence of user contact by inducing electrostatic electricity through the medium of a human body of the user.

In more detail, as can be seen from FIG. 7, the contact sensing portion 160 may include a coil through which a current flows.

For example, the contact sensing portion 160 may include a circular coil 111 on which conducting wires through which a current flows are thinly wound in the form of a circular shape. In addition, the contact sensing portion 160 may include a square coil 112 on which the conducting wires through which a current flows are thinly wound in the form of a square shape. However, the above-mentioned embodiment is merely an example of a physical structure of the coil, and may be applied to various shapes of coils as necessary.

In addition, the circular coil 111 and the square coil 112 may include a memory 111*a* and a memory 112*a*, respectively. The memories 111*a* and 112*a* of the contact sensing portion 160 may store various user-established functions of the ultrasonic probe 100 therein. The memories 111*a* and 112*a* of the contact sensing portion 160 may store various operations corresponding to a combination of the contact sensing results of the contact sensing portion 160. The operation corresponding to a combination of the contact sensing results may include at least one of Region of Interest (ROI) selection regarding the target object, ultrasonic image freezing, ultrasonic image capture, measurement data acquisition, Time Gain Compensation (TGC) control, Lateral Gain Compensation (LGC) control, ultrasonic image depth control, 2D/3D image conversion, and focusing. In addition, the scope or spirit of the memories 111*a* and 112*a* of the contact sensing portion 160 are not limited thereto, and the memories 111*a* and 112*a* may store many more functions therein. A detailed description thereof will hereinafter be given with reference to FIG. 11.

The coil of the contact sensing portion 160 may receive a current from at least one of a power-supply portion 900 of the main body and a battery 170 contained in the ultrasonic probe 100. In this case, magnetic flux may occur because current flows through the coil, resulting in occurrence of electrons or electromagnetic force. In addition, the human body is a conductor through which current flows, such that the contact sensing portion 160 may detect the presence or absence of user contact by detecting electrons or electromagnetic force induced by the coil. Therefore, the ultrasonic probe 100 may detect whether the user contacts a plurality of regions of the ultrasonic probe 100 through the medium of a human body of the user.

As described above, if the user contact is detected through the contact sensing portion 160 and the ultrasonic probe 100 is used as an input portion, a touch sensor for recognizing user touch, a pressure sensor for recognizing pressure applied by the user, etc. need not be constructed. Therefore, the ultrasonic probe 100 may be configured to easily recognize user contact using the contact sensing portion 160 without using a high-priced sensor or a separate device, such that the ultrasonic probe 100 may be used as an input portion.

The contact sensing part 160 may include a first contact sensing portion 161, a second contact sensing portion 162, a third contact sensing portion 163, and a fourth contact sensing portion 164. In addition, at least one of the first contact sensing portion 161, the second contact sensing portion 162, and the third contact sensing portion 163 may be formed of an electrically conductive material, and may include at least two sub-regions configured to detect user contact. However, the above-mentioned example is an example of the contact sensing portion 160 formed over the ultrasonic probe 100. If a surface region of the ultrasonic probe 100 is divided into a plurality of sub-regions, many more contact sensing portions may also be formed as necessary. The scope or spirit of the present disclosure is not limited to four contact sensing portions 160 as described above. In addition, the surfaces of at least two of the first contact sensing portion 161, the second contact sensing portion 162, the third contact sensing portion 163, and the fourth contact sensing portion 164 may be formed of different materials. Therefore, when the user grasps the ultrasonic probe 100, the user may make a distinction among the first contact sensing portion 161, the second contact sensing portion 162, the third contact sensing portion 163, and the fourth contact sensing portion 164.

The first contact sensing portion 161, the second contact sensing portion 162, the third contact sensing portion 163, and the fourth contact sensing portion 164 may be visually distinguished from one another using at least one of a symbol, a letter, a figure, a shape, a color, and a 3D structure. Therefore, the user may visually or tactually identify each region of the contact sensing portion 160 of the ultrasonic probe 100, such that the user may easily and conveniently use functions of the ultrasonic probe 100.

The first contact sensing portion 161 and the second contact sensing portion 162 may be electrically coupled to each other by user contact. In addition, at least two of the first contact sensing portion 161, the second contact sensing portion 162, the third contact sensing portion 163, and the fourth contact sensing portion 164 may also be electrically coupled to each other by user contact.

The user may generally grasp the ultrasonic probe 100 as illustrated in FIG. 6. As a result, the first contact sensing portion 161 and the second contact sensing portion 162 may be electrically coupled to each other by user contact through the medium of a human body of the user.

In more detail, since the user's hand serves as a passage of electrons (e), the ultrasonic probe 100 may recognize that some regions of the first contact sensing portion 161 are electrically coupled to some regions of the second contact sensing portion 162. A detailed description thereof has already been disclosed, and will herein be omitted for convenience of description.

In this way, the ultrasonic probe 100 may detect a first contact at the first contact sensing portion 161 and a second contact at the second contact sensing portion 162.

Although the above-mentioned example has exemplarily disclosed only the first contact at the first contact sensing portion 161 and the second contact at the second contact sensing portion 162 for convenience of description, the scope or spirit of the present disclosure is not limited thereto, and the above example may also be applied to all constituent structures of the contact sensing portion 160.

Referring to FIG. 8, the first contact sensing portion 161 may be installed at a single position of an outer surface of the housing (h) of FIG. 1, and may detect the presence or absence of user contact. In this case, the single position of the outer surface of the housing (h) may be a certain position of the ultrasonic probe 100. Generally, when the user grasps the ultrasonic probe 100 using his or her hand, the above single position of the outer surface of the housing (h) may indicate a wide region contacting the user's hand, without being limited thereto. In addition, the first contact sensing portion 161 may include a first sub contact sensing portion 101 and a second sub contact sensing portion 102.

The first sub contact sensing portion 101 may denote one surface of the first contact sensing portion 161, and the second sub contact sensing portion 102 may denote the remaining surfaces other than the first sub contact sensing portion 101 of the first contact sensing portion 161.

The first sub contact sensing portion 101 and the second sub contact sensing portion 102 may detect user contact. User contact detected by the first sub contact sensing portion 101 may be different from user contact detected by the second sub contact sensing portion 102. In addition, according to a structure in which the first contact sensing portion 161 includes the first sub contact sensing portion 101 and the second sub contact sensing portion 102, a contact surface may be changed in different ways according to user's grasping methods, such that different contact surfaces may be reflected in the above structure.

In more detail, the first contact sensing portion 161 may be classified into the first sub contact sensing portion 101 and the second sub contact sensing portion 102. The first sub contact sensing portion 101 and the second sub contact sensing portion 102 may detect user contact. In more detail, the contact surface may correspond to the first sub contact sensing portion 101 or the second sub contact sensing portion 102 according to whether the user is a left-handed person or a right-handed person, such that the first contact sensing portion 161 may recognize the contact surface in different ways according to the first sub contact sensing portion 101 and the second sub contact sensing portion 102.

Accordingly, even when the user turns the ultrasonic probe 100 over and grasps the overturned ultrasonic probe 100, the first contact sensing portion 161 may recognize such contact as the same user contact as in the above example, and may thus perform the same function. If necessary, the first contact sensing portion 161 may recognize such contact as a different user contact, and may thus perform a different function.

The second contact sensing portion 162 may be arranged at a different position from the first contact sensing portion, such that the second contact sensing portion 162 may detect user contact. In addition, the second contact sensing portion 162 may include a third sub contact sensing portion 105 and a fourth sub contact sensing portion 106.

The third sub contact sensing portion 105 may denote one surface of the second contact sensing portion 162, and the fourth sub contact sensing portion 106 may denote the remaining surfaces other than the third sub contact sensing portion 105 of the second contact sensing portion 162. The third sub contact sensing portion 105 and the fourth sub contact sensing portion 106 may detect user contact. User contact detected by the third sub contact sensing portion 105 may be different from user contact detected by the fourth sub contact sensing portion 106.

The third contact sensing portion 163 may be formed between the first contact sensing portion 161 and the second contact sensing portion 162, and may include a plurality of sub contact sensing portions 103 and 104 sequentially formed.

In more detail, the plurality of sub contact sensing portions 103 and 104 may be sequentially formed between the first contact sensing portion 161 and the second contact sensing portion 162, and may construct a plurality of lines. Each line of the plurality of sub contact sensing portions 103 and 104 may be used to detect user contact. In addition, the plurality of sub contact sensing portions 103 and 104 may identify user contact detected in each line, and may detect such user contact.

The sub contact sensing portions 103 and 104 may make a distinction among user contacts through a plurality of regions distinguished from one another by a plurality of lines shown in FIG. 8, and may detect different user contacts generated from the plurality of regions. In addition, the user may perform various functions of the ultrasonic probe 100 through the plurality of sub contact sensing portions 103 and 104. For example, the user may carry out various functions (e.g., gain control, TGC/LGC control, etc.) of the ultrasonic probe 100 by performing various operations (e.g., flicking operation, rolling operation, etc.) using an index finger of one hand grasping the ultrasonic probe 100 or using the other hand not grasping the ultrasonic probe 100.

The fourth contact sensing portion 164 may include a lens formed of an electrically conductive material, and may detect whether or not the user contacts the lens. That is, the fourth contact sensing portion 164 may detect the presence or absence of user contact through the lens. Most of the fourth contact sensing portion 164 may be formed of the lens, such that the fourth contact sensing portion 164 may detect whether the lens contacts the human body of the user, and may thus be applied to a control method of output signals including ultrasonic waves, laser light, etc. transmitted/received through the lens. For example, when the fourth contact sensing portion 164 detects the human body of the user, the ultrasonic probe 100 may operate. By application of the above operation, when the fourth contact sensing portion 164 begins to detect the human body of the user, a power-supply voltage is immediately supplied to the ultrasonic probe 100, such that power consumption of the ultrasonic imaging apparatus 10 may be reduced.

The first to fourth contact sensing portions 161 to 164 may detect user contact. In this case, user contacts detected by the first to fourth contact sensing portions 161 to 164 may be plural contacts but not a single contact, and may be different contacts. Therefore, the first to fourth contact sensing portions 161 to 164 may detect plural user contacts, and may discriminate among the user contacts.

The first to third contact sensing portions 161 to 163 may detect whether the user contacts the respective contact sensing portions. It is determined whether user contact is detected by at least two of the first to third contact sensing portions 161 to 163, such that an electrical connection state between the user's body and the contact sensing portions may be recognized. In other words, the first to third contact sensing portions 161 to 163 may be used to determine whether user contact is generated from at least two contact surfaces.

However, the fourth contact sensing portion 164 may independently detect a human body (e.g., a patient's body) in a different way from the first to third contact sensing portions 161 to 163. Therefore, the fourth contact sensing portion 164 may be used to detect only one contact surface instead of plural contact surfaces, irrespective of whether the user contacts the first to third contact sensing portions 161 to 163.

In addition, the first to fourth contact sensing portions 161 to 164 are classified into the plurality of regions as described above, and may detect user contacts on the respective regions. Therefore, the ultrasonic probe 100 may detect various and different user contacts using the first to fourth contact sensing portions 161 to 164. The ultrasonic probe 100 may determine a combination of different user contacts, and may perform the operation corresponding to the determined combination.

In more detail, the ultrasonic probe 100 may determine a combination of the contact sensing results of the first and second contact sensing portions 161 and 162, and may perform the operation corresponding to the determined combination of the contact sensing results. In addition, the ultrasonic probe 100 may perform the operation corresponding to a combination of the contact sensing results of at least two of the first to fourth contact sensing portions 161, 162, 163, and 164. A detailed description thereof will hereinafter be described with reference to FIG. 11.

In addition, a combination of the contact sensing results may be determined using at least one of a contact position, a contact time, and the order of contacts. For example, assuming that the combination of the contact sensing results is the order of contacts, when the first contact sensing portion 161 of the ultrasonic probe 100 first detects user contact and the second contact sensing portion 162 then detects such user contact, the order of contacts is denoted by "the first contact sensing portion 161→the second contact sensing portion 162". As a result, the ultrasonic probe 100 may perform a specific operation corresponding to a combination of the contact sensing results related to the order of contacts. Here, if the specific operation is set to a freeze function, the ultrasonic probe 100 may freeze a current ultrasonic image of the target object. In addition, if the combination of the contact sensing results is determined to be the contact position, the ultrasonic probe 100 does not perform the freeze function even though user contact is detected according to the aforementioned order of contacts, and may perform an operation corresponding to a combination of contact sensing results of the contact position. However, the above-mentioned example illustrates an exemplary combination of the contact sensing results, the scope or spirit of the present disclosure is not limited thereto, and the above-mentioned example may also be applied to various combinations of the contact sensing results.

The operation corresponding to a combination of the contact sensing results may include at least one of Region of Interest (ROI) selection regarding the target object, ultrasonic image freezing, ultrasonic image capture, measurement data acquisition, Time Gain Compensation (TGC) control, Lateral Gain Compensation (LGC) control, ultrasonic image depth control, 2D/3D image conversion, and focusing, without being limited thereto. Generally, the above-mentioned operation may include all functions capable of being performed by the ultrasonic probe 100.

In addition, the operation corresponding to the combination of the contact sensing results may be established by the user. For example, assuming that a first contact of the first contact sensing portion 161 and a second contact of the second contact sensing portion 162 are sequentially detected, the user may decide to perform an ultrasonic image capture function of the ultrasonic probe 100. The user-established operation corresponding to the combination of the contact sensing results may be stored in a memory of the contact sensing portion 160 or in a storage 700 of the main body.

In addition, the contact sensing portion 160 may detect user contact, may convert information regarding a combination of the detected contact sensing results into an electrical signal, and may transmit the electrical signal to a controller 240. In the above-mentioned example, because the controller 240 is contained in the main body 200, the electrical signal indicating information of the combination of the contact sensing results acquired by the contact sensing portion 160 of the ultrasonic probe 100 can be transmitted to the controller 240. In contrast, if at least one processor is contained in the ultrasonic probe 100 and the ultrasonic probe 100 is controlled by the processor contained in the ultrasonic probe 100, information regarding a combination of contact sensing results obtained by the contact sensing portion 160 of the ultrasonic probe 100 may also be transmitted to the processor contained in the ultrasonic probe 100.

The battery 170 may be contained in the ultrasonic probe 100, such that the battery 170 may provide a current to the coil of the contact sensing portion 160 or may provide a power source to various constituent elements contained in the ultrasonic probe 100.

The processor 180 may receive information regarding user contact from the plurality of contact sensing portions 160 of the ultrasonic probe 100, and may determine a combination of the contact sensing results through various received contacts. The processor 180 may control the ultrasonic probe 100 to perform the ultrasonic probe 100's operation stored in the memories 111a and 112a installed at the coil of the contact sensing portion 160. The processor 180 may also control the ultrasonic probe 100 to perform an operation corresponding to a combination of user-established contact sensing results. That is, at least one processor 180 is contained in the ultrasonic probe 100, such that the ultrasonic probe 100 may detect user contact through the contact sensing portion 160 and may perform an operation corresponding to a combination of the detected contact sensing results.

The main body 200 may include various constituent elements needed to control the ultrasonic probe 100 or to generate an ultrasonic image on the basis of the signal received from the ultrasonic probe 100, and may be connected to the ultrasonic probe 100 through the cable 120.

In addition, the ultrasonic probe 100 may include one or more processors. Therefore, the ultrasonic probe 100 may include at least one processor acting as the controller contained in the main body 200, and may also be controlled in a different way from the controller 240 of the ultrasonic imaging apparatus 10.

Not only a signal processor 220, an image processor 230, and a controller 240 contained in the main body 200, but also a display 300, an input portion 400, a notification portion 500, a communicator 600, a storage 700, and a power-supply portion 900 will hereinafter be described with reference to the attached drawings. In addition, the main body 200 may further include the display 300, the input portion 400, the notification portion 500, the communicator 600, the storage 700, and the power-supply portion 900, or may be constructed independently. If the above-mentioned constituent elements of the latter case are identical in structure to those of the former case, a detailed description thereof will herein be omitted for convenience of description.

The signal processor 220 may convert a focused digital signal received from the ultrasonic probe 100 into a signal appropriate for image processing. For example, the signal processor 220 may perform filtering to remove a noise signal other than a desired frequency band.

The signal processor 220 may be implemented as a Digital Signal Processor (DSP), and may generate ultrasonic image data by performing envelope detection processing for detecting the magnitude of an echo ultrasonic signal on the basis of the focused digital signal.

The image processor 230 may generate an image on the basis of the ultrasonic image data generated by the signal processor 220, such that a user (e.g., a doctor or a patient) may view the generated image regarding the interior of the target object (ob) (e.g., a human body).

The image processor 230 may transmit the generated ultrasonic image to the display 300 using the ultrasonic image data.

In accordance with the embodiment, the image processor 230 may perform additional image processing for the ultrasonic image as necessary. The image processor 230 may further perform post-processing of the ultrasonic image. As an example of the post-processing, the image processor 230 may correct or readjust contrast, brightness, and sharpness of the ultrasonic image.

The additional image processing of the image processor 230 may be carried out according to predetermined setting information, or may be carried out by a user instruction or command received through the input portion 400.

The controller 240 may control at least one of the ultrasonic imaging apparatus 10 and the ultrasonic probe 100. For example, the controller 240 may control the signal processor 220, the image processor 230, the ultrasonic probe 100, and the display 300.

The controller 240 may receive information regarding the presence or absence of user contact from the ultrasonic probe 100. In addition, the controller 240 may receive an electrical signal indicating information of a combination of the detected contact sensing results from the ultrasonic probe 100. In more detail, the controller 240 may receive information regarding the presence or absence of user contact from the contact sensing portion 160 of the ultrasonic probe 100, and may determine the contact sensing result using the received information. Thereafter, the controller 240 may control at least one of the ultrasonic probe 100 and the ultrasonic imaging apparatus 10 so as to perform an operation corresponding to the determined contact sensing result. Therefore, according to a control command of the controller 240, at least one of the ultrasonic probe 100 and the ultrasonic imaging apparatus 10 may perform the operation corresponding to a combination of the contact sensing results. A detailed description thereof will hereinafter be described with reference to FIG. 11.

In addition, because the controller 240 is contained in the main body 200, an electrical signal indicating information of the combination of the contact sensing results acquired by the contact sensing portion 160 of the ultrasonic probe 100 can be transmitted to the controller 240. In contrast, if at least one processor is contained in the ultrasonic probe 100 and the ultrasonic probe 100 is controlled by the processor contained in the ultrasonic probe 100, information regarding a combination of the contact sensing results obtained by the contact sensing portion 160 of the ultrasonic probe 100 may also be transmitted to the processor contained in the ultrasonic probe 100.

The controller 240 may transmit and receive information regarding the combination of the contact sensing results obtained by the contact sensing portion 160 of the ultrasonic probe 100 to and from the communicator 600.

The controller 240 may control the storage 700 to store information regarding the combination of the contact sensing results obtained by the contact sensing portion 160 of the ultrasonic probe 100.

The controller 240 may transmit at least one of information regarding the presence or absence of user contact acquired from the contact sensing portion 160 of the ultrasonic probe 100 and the other information regarding the combination of the contact sensing results to the display 300.

In accordance with one embodiment, the controller 240 may control the ultrasonic imaging apparatus 10 according to the predetermined setting information, or may generate a predetermined control command according to a user instruction or command received through the input portion 400 and may then control the ultrasonic imaging apparatus 10.

The controller 240 may control not only the ultrasonic imaging apparatus 10 but also the ultrasonic probe 100. If the controller 240 is paired with the external device using wireless communication, Bluetooth, NFC, IrDA, etc. the controller 240 may control at least one of the ultrasonic imaging apparatus 10 and the ultrasonic probe 100 through the external device. In addition, the controller 240 may control the communicator 600 to transmit various kinds of information regarding the ultrasonic imaging apparatus 10 to the external device.

The controller 240 may include a read only memory (ROM) and a random access memory (RAM). The ROM may store control programs for controlling the processor and ultrasonic imaging apparatus 10 therein. The RAM may store signals or ultrasonic image data received from either the ultrasonic probe 100 or the input portion 400 of the ultrasonic imaging apparatus 10, or may be used as a storage region corresponding to various tasks executed by the ultrasonic imaging apparatus 10. In addition, although the controller 240 of the embodiment is contained in the main body 200, the scope or spirit of the present disclosure is not limited thereto, and the controller 240 may also be contained in the ultrasonic probe 100 as necessary. The controller 240 may include one or more processors.

A separate circuit board electrically coupled to the controller 240 may include a graphic processing board including a processor and a RAM or ROM.

The processor, the RAM, and the ROM may be coupled to one another through an internal bus.

The controller 240 may refer to a term indicating a constituent element including the processor, the RAM, and the ROM.

The processor 240 may refer to a term indicating a constituent element including the processor, the RAM, the ROM, and the processing board.

The display 300 may display various kinds of information received from the controller 240. The display 300 may display text or image data indicating at least one of information regarding the presence or absence of user contact acquired by the contact sensing portion 160 of the ultrasonic probe 100 and the other information regarding the combination of the contact sensing results. As a result, the user who views the text or image data may easily recognize a shape of his or her hand grasping the ultrasonic probe 100, and may also easily recognize which one of parts of the contact sensing portion 160 contacts the user hand.

In addition, the display 300 may display at least one of an ultrasonic image acquired by the ultrasonic probe 100 and ultrasonic image information.

The display 300 may display an ultrasonic image generated by the image processor 230 in such a manner that the user may visually recognize the internal structure or tissues of the target object (ob). The display 300 may display various data and images in association with the ultrasonic imaging apparatus 10.

In more detail, the display 300 may simultaneously display not only the internal structure or tissues of the target object (ob) but also elasticity of the region of interest (ROI) of the target object (ob), such that the user may visually recognize images of the target object (ob) and may numerically confirm the images of the target object (ob).

The display 300 may be implemented by any well-known display panel, for example, a Cathode Ray Tube (CRT), a Liquid Crystal Display (LCD), a Light Emitting Diode (LED), a Plasma Display Panel (PDP), an Organic Light Emitting Diode (OLED), etc., without being limited thereto.

If the display 300 is implemented as a touchscreen, the display 300 may also act as the input portion 400. That is, the main body 200 may receive various commands from the user through at least one of the display 300 and the input portion 400.

If the display 300 is used as the input portion 400, the display 300 may display at least one of a UI (User Interface) screen image and a selection screen image through which the user can input a command. In this case, the user may touch at least one of an icon, an image, and text displayed on the display 300, such that the corresponding function of at least one of the ultrasonic imaging apparatus 10 and the ultrasonic probe 100 can be carried out.

In more detail, if the display 300 acts as a touchscreen, the display 300 may display at least one of icon, image, and text, which are needed to add annotation or comments to ultrasonic images and measurement data, as well as to perform focusing, TGC/LGC control, zoom-in/zoom-out, rotation, 2D/3D conversion, etc. of the ultrasonic images and measurement data. In this case, since the display 300 includes the touchscreen function, the user may select at least one of icon, image, and text displayed on the display 300 in a manner that the ultrasonic imaging apparatus 10's function corresponding to at least one of icon, image, and text can be carried out.

Although not shown in the drawings, the main body 200 may include a voice recognition sensor such that the main body 200 may receive a voice command from the user through the voice recognition sensor.

The display 300 may display an ultrasonic image regarding a target site contained in the target object. The ultrasonic image displayed on the display 300 may be a 2D ultrasonic image or a 3D ultrasonic image, and may display various ultrasonic images according to operation modes of the ultrasonic imaging apparatus 10. The display 300 may display not only menu or information needed for ultrasound diagnosis but also information regarding operation states of the ultrasonic probe 100.

In accordance with one embodiment, the ultrasonic image may include an amplitude mode (A-mode) image, a brightness mode (B-mode) image, a motion mode (M-mode) image, a color mode (C-mode) image, and a Doppler mode (D-mode) image.

The A-mode image may refer to an ultrasonic image indicating the amplitude of an ultrasonic signal corresponding to an echo ultrasonic signal. The B-mode image may refer to an ultrasonic image in which the amplitude of the ultrasonic signal corresponding to the echo ultrasonic signal is represented as brightness. The M-mode image may refer to an ultrasonic image indicating movement of a target object according to lapse of time at a specific position. The D-mode image may refer to an ultrasonic image may refer to an ultrasonic image in which a moving target object is represented as a waveform shape using the Doppler effect. The C-mode image may refer to an ultrasonic image for indicating the moving target object using a color spectrum.

The input portion 400 may receive not only the setting information related to the ultrasonic probe 100 but also various control commands from the user.

The input portion 400 may receive at least one of a command for performing various operations of the ultrasonic imaging apparatus 10 and the other command for changing the setting information related to the ultrasonic probe 100.

In accordance with one embodiment, the setting information related to the ultrasonic probe 100 may include gain information, zoom information, focus information, TGC information, depth information, frequency information, power information, frame average information, dynamic range information, etc. However, the setting information related to the ultrasonic probe 100 is not limited thereto, and may include various kinds of information capable of being established to capture ultrasonic images.

The above-mentioned information may be transferred to the ultrasonic probe 100 over a wired or wireless communication network, and the ultrasonic probe 100 may be established according to the received information. The main body 200 may receive various control commands (e.g., a command for transmitting the ultrasonic signal) from the user through the input portion 400, and may transmit the received control commands to the ultrasonic probe 100.

Meanwhile, the input portion 400 may also be implemented as a mouse, a keyboard, a foot switch, or a foot pedal. For example, the keyboard may be implemented by hardware. The keyboard may include at least one of a switch, a key, a joystick, a trackball, etc. In another example, the keyboard may also be implemented by software such as a graphical user interface (GUI). In this case, the keyboard may be displayed on the display 300. The foot switch or the foot pedal may be located below the main body 200, and the user may control the ultrasonic imaging apparatus 10 using the foot pedal.

One or more female connectors 201 (see FIG. 1) may be contained in the main body 200, and the female connector 201 may be connected to the ultrasonic probe 100 through the cable 120 and the male connector 130.

The input portion 400 may receive an instruction or command from the user so as to control the ultrasonic imaging apparatus 10. For example, the input portion 400 may include a user interface (UI), for example, a keyboard, a mouse, a trackball, a touchscreen, and an input button or paddle mounted to the ultrasonic probe 100.

If user contact is detected by the contact sensing portion 160 of the ultrasonic probe 100, the notification portion may inform the user of the detected user contact. The notification portion 500 may make a distinction among different contacts detected by the contact sensing portion 160, and may inform the user of the different contacts. In more detail, the notification portion 500 may audibly or visually inform the user of specific information as to whether the user contacts the contact sensing portion 160 using at least one of vibration, sound, a symbol, a letter, a figure, and a 3D structure. In addition, the notification portion 500 is contained in the main body 200 so that the notification portion 500 may output notification information through the speaker or the display 300. However, the scope or spirit of the present disclosure is not limited thereto, and the notification portion 500 may also be contained in the ultrasonic probe 100.

The communicator 600 may wirelessly communicate with at least one of the external device and the ultrasonic probe 100. The communicator 600 may transmit and receive data related to target object diagnosis, for example, an ultrasonic image, an echo ultrasonic signal, Doppler data, shear wave data, acquired through the ultrasonic probe 100. The communicator 600 may receive a variety of information from the external device. Here, the external device may include a wearable terminal, a wireless communication terminal, a smartphone, etc.

The storage 700 may store information regarding the operation corresponding to the contact sensing result detected by the contact sensing portion 160 of the ultrasonic probe 100. If the operation corresponding to a combination of the contact sensing results is established by the user, the storage 700 may store the established operation therein. The storage 700 may store at least one of an ultrasonic image of the target object acquired by the ultrasonic probe 100, diagnosis data related to the ultrasonic image, etc. The storage 700 may store various setting items related to the ultrasonic imaging apparatus 10. The storage portion 700 may be configured as at least one of a flash memory type, a hard disk type, a multimedia card micro card, a card type memory (e.g. a Secure Digital (SD) memory or an eXtreme Digital (XD) memory), a Random Access Memory (RAM), a Read Only Memory (ROM), an Electrically Erasable Programmable Read Only Memory (EEPROM), a Programmable Read Only Memory (PROM), a magnetic memory, a magnetic disk, an optical disc, etc. without being limited thereto.

The power-supply portion 900 may provide a power-supply signal to the respective constituent elements of the ultrasonic imaging apparatus 10 or the ultrasonic probe 10. In more detail, when the main body 200 is electrically coupled to the ultrasonic probe by wire, the power-supply portion 900 may provide a current to the contact sensing portion 160 of the ultrasonic probe 100. The contact sensing portion 160 of the ultrasonic probe 100 may detect user contact using a current received from the power-supply portion 900, and a detailed description thereof will herein be omitted for convenience of description.

The structures and operations of the ultrasonic imaging apparatus 10 and the ultrasonic probe 100 including the contact sensing portion have been disclosed with reference to FIGS. 5 to 8. A method for detecting user contact through the ultrasonic probe 100 and performing the corresponding operation on the basis of the contact sensing result according to the embodiment will hereinafter be described.

Figure 9:
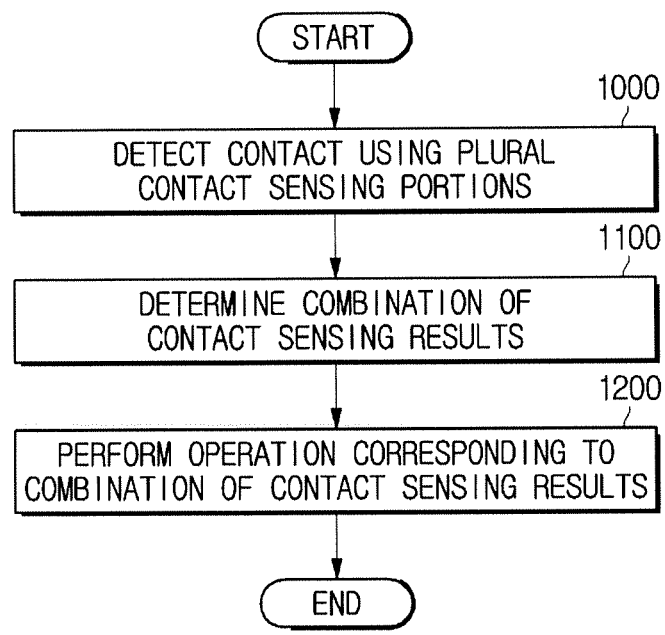
FIG. 9 is a flowchart illustrating a method for operating the ultrasonic probe according to a contact sensing result of the ultrasonic probe.
Figure 10:
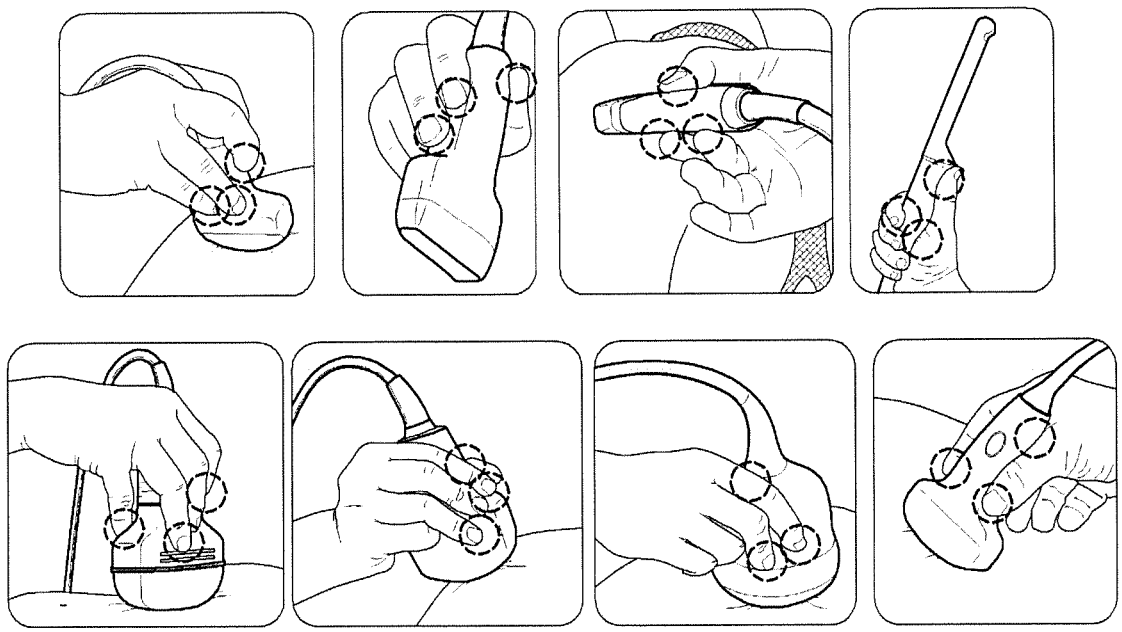
FIG. 10 is a conceptual diagram illustrating the plurality of contact portions grasped by any hand of a user.

FIG. 9 is a flowchart illustrating a method for operating the ultrasonic probe according to the contact sensing result of the ultrasonic probe. FIG. 10 is a conceptual diagram illustrating the plurality of contact portions grasped by any hand of a user. FIG. 11 illustrates exemplary operations corresponding to the contact sensing results of the plurality of contact portions.

A method for controlling the ultrasonic probe 100 to detect user contact through the contact sensing portion 160, and performing the operation corresponding to the detected contact sensing result according to the embodiment will hereinafter be described with reference to FIGS. 9 to 11.

The ultrasonic probe 100 may include a plurality of contact sensing portions 160, and may detect user contact through the plurality of contact sensing portions 160 (Operation 1000). The contact sensing portions 160 of the ultrasonic probe 100 may include a first contact sensing portion 161, a second contact sensing portion 162, a third contact sensing portion 163, and a fourth contact sensing portion 164, as described above. Each of the first contact sensing portion 161, the second contact sensing portion 162, the third contact sensing portion 163, and the fourth contact sensing portion 164 may include a plurality of regions to detect user contact in different ways.

As described above, the outer surface of the ultrasonic probe 100 may be formed of an electrically conductive material, resulting in occurrence of electrostatic induction. At least two of the plurality of contact sensing portions 160 may be electrically connected to each other through a human body of the user. If the at least two of the plurality of contact sensing portions 160 are electrically coupled to each other, the ultrasonic probe 100 may recognize detection of user contact.

In more detail, the ultrasonic probe 100 may detect a first contact in a first region of the outer surface of the ultrasonic probe 100 through the first contact sensing portion 161 of the ultrasonic probe 100. In addition, the ultrasonic probe 100 may detect a second contact in a second region different from one position of the outer surface of the ultrasonic probe 100 through the second contact sensing portion 162 of the ultrasonic probe 100. In addition, the ultrasonic probe 100 may detect a third contact using the third contact sensing portion 163 of the ultrasonic probe 100 in a region disposed between the first region and the second region. In addition, the ultrasonic probe 100 may detect a fourth contact through the fourth contact sensing portion 164 including the lens formed of an electrically conductive material. The above-mentioned first contact, second contact, third contact, and fourth contact may denote different contacts.

The ultrasonic probe 100 may detect various contact combinations of the first contact, the second contact, the third contact, and the fourth contact on the contact sensing portions 160.

For example, the user may grasp the ultrasonic probe 100 in various ways as shown in FIG. 10, and may create a combination of various contact sensing results obtained by at least two of contact detection of the first contact sensing portion 161, contact detection of the second contact sensing portion 162, contact detection of the third contact sensing portion 163, and contact detection of the fourth contact sensing portion 164. The combination of various contact sensing results may indicate that various input methods can be applied to the ultrasonic probe 100. In addition, the combination of the contact sensing results may be established in various ways by the user using at least one of a contact position, a contact time, and the order of contacts.

By various methods for controlling the user to grasp the contact sensing portions 160 in different ways, the user may input a control command corresponding to a combination of various contacts to the ultrasonic probe 100.

The ultrasonic probe 100 may detect user contact through the plurality of contact sensing portions 160, and may include a processor 180 for determining a combination of the detected contact sensing results. Therefore, the ultrasonic probe 100 may determine a combination of at least two of the first contact, the second contact, the third contact, and the fourth contact detected by the plurality of contact sensing portions 160. In addition, the ultrasonic probe 100 may determine whether the determined combination is a combination of user-established contact sensing results (Operation 1100).

As disclosed in the above example, the ultrasonic probe 100 detects user contact through the plurality of contact sensing portions 160, and the processor for determining the combination of the contact sensing results is contained in the ultrasonic probe 100.

In addition, the above-mentioned operation may also be achieved by the controller 240 of the main body 200. In more detail, the controller 240 may receive information regarding user contact from the contact sensing portions 160 of the ultrasonic probe 100, and may determine a combination of the contact sensing results. The controller 240 may also determine whether the determined combination is a combination of user-established contact sensing results (Operation 1100).

The ultrasonic probe 100 may perform the operation corresponding to the determined combination of the contact sensing results. The ultrasonic probe 100 may perform the operation corresponding to the combination of user-established contact sensing results (Operation 1200).

For example, as can be seen from FIG. 11, under the condition that the user grasps the ultrasonic probe 100, assuming that the ultrasonic probe 100 detects a contact generated in the first region of the first contact sensing portion 161 and then detects a contact generated in the second region of the second contact sensing portion 162 in a different way from the first region of the first contact sensing portion 161, this means that a combination of the contact sensing results between the first contact of the first contact sensing portion 161 and the second contact of the second contact sensing portion 162 has occurred. Therefore, the ultrasonic probe 100 may perform the ROI operation corresponding to the combination of the contact sensing results between the first and second contacts established by the user. In this case, it is understood that the combination of the contact sensing results is established according to the order of contacts.

In another example, under the condition that the user grasps the ultrasonic probe 100, assuming that the ultrasonic probe 100 detects a contact generated in the first region of the first contact sensing portion 161 and then detects a contact generated in the third region of the third contact sensing portion 163 in a different way from the first region of the first contact sensing portion 161, this means that a combination of the contact sensing results between the first contact of the first contact sensing portion 161 and the third contact of the third contact sensing portion 163 has occurred. Therefore, the ultrasonic probe 100 may perform a TGC/LGC control operation corresponding to a combination of the contact sensing results between the first and third contacts established by the user.

In the last example, under the condition that the user grasps the ultrasonic probe 100, assuming that the ultrasonic probe 100 detects a contact generated in the first region of the first contact sensing portion 161, detects a contact generated in the second region of the second contact sensing portion 162, and finally detects a contact generated in the third region of the third contact sensing portion 163, the ultrasonic probe 100 may determine the occurrence of a combination of the first contact of the first contact sensing portion 161, the second contact of the second contact sensing portion 152, and the third contact of the third contact sensing portion 163. Therefore, the ultrasonic probe 100 may perform a freeze operation corresponding to the combination of the first to third contacts established by the user. The above-mentioned example has disclosed that the combination of the contact sensing results is determined to be a contact position and the order of contacts for convenience of description. The scope or spirit of the ultrasonic probe 100 may perform various operations according to various combinations of the contact sensing results.

The ultrasonic probe for detecting user contact using the plurality of contact sensing portions, determining a combination of the contact sensing results established by the user, and performing the operation corresponding to the determined combination of the contact sensing results, the method for controlling the ultrasonic probe, and the ultrasonic imaging apparatus including the ultrasonic probe according to the embodiments of the present disclosure have been disclosed above.

As is apparent from the above description, the ultrasonic probe, the method for controlling the ultrasonic probe, and the ultrasonic imaging apparatus including the ultrasonic probe according to the embodiments may input various control commands using the ultrasonic probe as an input portion.

In addition, when the ultrasonic probe is used as the input portion, the ultrasonic probe is electrically coupled to the contact sensing portion formed of an electrically conductive material through a human body in a manner that control commands are input to the ultrasonic imaging apparatus through the contact sensing portion. As a result, the ultrasonic probe need not include a separate sensor (for example, a touch sensor, a pressure sensor, a sensing sensor, etc.), resulting in reduction of production costs of the ultrasonic probe.

The above-mentioned embodiments are merely exemplary for better understanding of the present disclosure, and the scope of the present disclosure is not limited thereto. For example, a single component may be divided into two or more components, or two or more components may be combined into a single component as needed.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An ultrasonic probe comprising:
  a housing;
  a first contact sensing portion including an electrically conductive material, located at one position of an outer surface of the housing, and configured to detect a first contact in the first contact sensing portion;
  a second contact sensing portion including an electrically conductive material, located at a different position from the first contact sensing portion, and configured to detect a second contact in the second contact sensing portion; and
  a processor configured to:
    detect an electrical connection between the first and second contact sensing portions, the electrical connection being made outside the ultrasonic probe by the first and second contacts, the electrical connection representing contact sensing results obtained from the first contact sensing portion and the second contact sensing portion, and
    control the ultrasonic probe to perform an operation which is determined based on a contact order between the first contact sensing portion and the second contact sensing portion.

2. The ultrasonic probe according to claim 1, further comprising at least one of:
  a third contact sensing portion formed between the first contact sensing portion and the second contact sensing portion, and configured to include a plurality of sub contact sensing portions sequentially formed; and
  a fourth contact sensing portion formed of an electrically conductive material.

3. The ultrasonic probe according to claim 2, wherein:
  an operation corresponding to a combination of contact sensing results of at least two from among the first contact sensing portion, the second contact sensing portion, the third contact sensing portion, and the fourth contact sensing portion is carried out.

4. The ultrasonic probe according to claim 2, wherein:
  at least one of the first contact sensing portion, the second contact sensing portion, and the third contact sensing portion includes at least two sub regions, each of which is formed of an electrically conductive material and detects presence or absence of contact.

5. The ultrasonic probe according to claim 1, wherein the operation corresponding to the combination of the contact sensing results includes at least one of Region of Interest (ROI) selection regarding a target object, ultrasonic image freeze, ultrasonic image capture, measurement data acquisition, Time Gain Compensation (TGC) control, Lateral Gain Compensation (LGC) control, ultrasonic image depth control, 2D/3D image conversion, focusing, and probe automatic selection.

6. The ultrasonic probe according to claim 1, wherein the combination of the contact sensing results is determined using at least one of a contact position, a contact time, and an order of contacts.

7. The ultrasonic probe according to claim 1, wherein the operation corresponding to the combination of the contact sensing results is established by a user or is predetermined by the user.

8. The ultrasonic probe according to claim 2, wherein:
  surfaces of at least two of the first contact sensing portion, the second contact sensing portion, the third contact sensing portion, and the fourth contact sensing portion are formed of different materials.

9. The ultrasonic probe according to claim 2, wherein the first contact sensing portion, the second contact sensing portion, the third contact sensing portion, and the fourth contact sensing portion are visually distinguished from one another using at least one of a symbol, a letter, a figure, a shape, a color, and a solid structure.

10. A method for controlling an ultrasonic probe comprising:
  detecting a first contact in a first region of an outer surface of the ultrasonic probe;
  detecting a second contact in a second region different from one position of the outer surface of the ultrasonic probe;

detecting an electrical connection between the first region and the second region, the electrical connection being made outside the ultrasonic probe by the first and second contacts, the electrical connection representing contact sensing results obtained from the first region and the second region; and controlling the ultrasonic probe to perform an operation which is determined based on a contact order between the first and second regions.

11. The method according to claim 10, further comprising:

detecting a third contact in a region disposed between the first region and the second region.

12. The method according to claim 11, further comprising:

detecting a fourth contact using a contact sensing portion formed of an electrically conductive material.

13. The method according to claim 12, further comprising:

determining a combination of contact sensing results of at least two from among the first contact, the second contact, the third contact, and the fourth contact, and performing an operation corresponding to the determined combination.

14. The method according to claim 10, wherein the controlling of the ultrasonic probe to perform the operation corresponding to the determined combination of the contact sensing results includes at least one of:

selecting a Region of Interest (ROI) regarding a target object;
freezing an ultrasonic image;
capturing the ultrasonic image;
acquiring measurement data;
controlling Time Gain Compensation (TGC);
controlling Lateral Gain Compensation (LGC);
controlling depth of the ultrasonic image;
performing 2D/3D image conversion;
focusing the ultrasonic image; and
automatically selecting a probe.

15. The method according to claim 10, wherein the combination of the contact sensing results is determined using at least one of a contact position, a contact time, and an order of contacts.

16. The method according to claim 10, wherein the operation corresponding to the combination of the contact sensing results is established by a user.

17. The method according to claim 10, wherein:

the first region of the outer surface of the ultrasonic probe and the second region different from one position of the outer surface of the ultrasonic probe are formed of different materials.

18. The method according to claim 10, wherein the first region of the outer surface of the ultrasonic probe and the second region different from one position of the outer surface of the ultrasonic probe are visually distinguished from each other using at least one of a symbol, a letter, a figure, a shape, a color, and a solid structure.

19. An ultrasonic imaging apparatus comprising:

an ultrasonic probe including a housing;
a first contact sensing portion including an electrically conductive material, located at one position of an outer surface of the housing, and configured to detect a first contact in the first contact sensing portion; and
a second contact sensing portion including an electrically conductive material, located at a different position from the first contact sensing portion, and configured to detect a second contact in the second contact sensing portion; and
a controller configured to:
detect an electrical connection between the first and second contact sensing portions, the electrical connection being made outside the ultrasonic probe by the first and second contacts, the electrical connection representing contact sensing results obtained from the first contact sensing portion and the second contact sensing portion, and
control the ultrasonic probe to perform an operation which is determined based on a contact order between the first contact sensing portion and the second contact sensing portion.

* * * * *